United States Patent
Noda et al.

(10) Patent No.: US 6,454,792 B1
(45) Date of Patent: Sep. 24, 2002

(54) COOLING SYSTEM FOR INDWELLING HEAT EXCHANGE CATHETER

(75) Inventors: Wayne A. Noda, Mission Viejo, CA (US); William J. Worthen, Coto De Caza, CA (US)

(73) Assignee: Alsius Corporation, Irvine, CA (US)

( * ) Notice: Subject to any disclaimer, the term of this patent is extended or adjusted under 35 U.S.C. 154(b) by 121 days.

(21) Appl. No.: 09/697,667

(22) Filed: Oct. 25, 2000

Related U.S. Application Data (63) Continuation of application No. 09/220,897, filed on Dec. 24, 1998, now Pat. No. 6,146,411.

(51) Int. Cl.[7] .................................................. A61F 7/00

(52) U.S. Cl. ........................................ 607/105; 607/96

(58) Field of Search ........................ 607/96, 104, 105, 607/113

(56) References Cited

U.S. PATENT DOCUMENTS

| | | |
|---|---|---|
| 2,058,780 A | 10/1936 | Elliot |
| 2,077,453 A | 4/1937 | Albright |
| 2,190,384 A | 2/1940 | Newman |
| 3,125,096 A | 3/1964 | Antiles et al. |
| 3,425,419 A | 2/1969 | Dato |
| 3,460,538 A | 8/1969 | Armstrong |
| 3,504,674 A * | 4/1970 | Swenson et al. ............ 607/105 |
| 4,014,317 A | 3/1977 | Bruno |
| 4,111,209 A | 9/1978 | Wolvek et al. |

(List continued on next page.)

FOREIGN PATENT DOCUMENTS

| | | |
|---|---|---|
| SU | 848031 | 10/1979 |
| WO | 84/02839 | 8/1984 |
| WO | 92/10227 | 6/1992 |

OTHER PUBLICATIONS

U.S. patent application Ser. No. 09/282,971, Philips, pending.
U.S. patent application Ser. No. 09/349,606, Balding, pending.
U.S. patent application Ser. No. 09/416,753, Evans et al., pending.
U.S. patent application Ser. No. 09/427,745, Pham et al., pending.
U.S. patent application Ser. No. 09/761,069, Whitebook et al., pending.
U.S. patent application Ser. No. 09/703,791, Evans et al., pending.
U.S. patent application Ser. No. 09/697,667, Noda et al., pending.
Jenkins et al.; Postbypass Hypothermia and its Relationship to the Energy Balance of Cardiopulmonary Bypass, Journal of Cardiothoracic and Vascular Anesthesia, Apr. 1991; vol. 5, No. 2, pp. 135–138.
White et al., Profound selective cooling and ischemia of primate brain without pump or oxygenator, Surgery, Jul. 1969, vol. 66, No.1, pp. 224–232.
Wright et al., Hypothermia Controlled Reperfusion: Two Non–Pharmacologic Methods Which Dimish Ischemia–Reperfusion Injury in Skeletal Muscle, Microcirc. Endoth., 1989, Lymphatics, vol. 5.

(List continued on next page.)

*Primary Examiner*—Roy D. Gibson
(74) *Attorney, Agent, or Firm*—Arlyn Alonzo; Burns Doane Swecker & Mathis (57) ABSTRACT

A system for exchanging heat with the body of a patient for cooling or warming the patient provides for automatic temperature control in accordance with the monitored temperature of the patient. The system comprises a temperature control module and temperature probes for making body core temperature measurements. The body core temperature measurements are used to control the temperature of fluid circulating within the fluid circuit.

12 Claims, 5 Drawing Sheets

U.S. PATENT DOCUMENTS

| | | |
|---|---|---|
| 4,181,132 A | 1/1980 | Parks |
| 4,298,006 A | 11/1981 | Parks |
| 4,312,364 A | 1/1982 | Convert et al. |
| 4,416,280 A | 11/1983 | Carpenter et al. |
| 4,445,886 A | 5/1984 | Osterholm |
| 4,638,436 A | 1/1987 | Badger et al. |
| 4,686,085 A | 8/1987 | Osterholm |
| 4,736,748 A | 4/1988 | Nakamura et al. |
| 4,804,358 A | 2/1989 | Karcher et al. |
| 4,819,655 A | 4/1989 | Webler |
| 4,850,969 A | 7/1989 | Jackson |
| 4,899,741 A | 2/1990 | Bentley et al. |
| 4,907,589 A | 3/1990 | Cosman |
| 4,917,667 A | 4/1990 | Jackson |
| 4,955,377 A | 9/1990 | Lewnnox et al. |
| 5,011,468 A | 4/1991 | Lundquist et al. |
| 5,059,167 A | 10/1991 | Lundquist et al. |
| 5,191,883 A | 3/1993 | Lennox et al. |
| 5,304,214 A | 4/1994 | DeFord et al. |
| 5,342,301 A | 8/1994 | Saab |
| 5,346,508 A | 9/1994 | Hastings |
| 5,354,277 A | 10/1994 | Guzman et al. |
| 5,385,540 A | 1/1995 | Abbott et al. |
| 5,411,477 A | 5/1995 | Saab |
| 5,433,740 A | 7/1995 | Yamaguchi |
| 5,437,673 A | 8/1995 | Baust et al. |
| 5,486,204 A | 1/1996 | Clifton |
| 5,486,208 A | 1/1996 | Ginsburg |
| 5,549,559 A | 8/1996 | Eshel |
| 5,624,392 A | 4/1997 | Saab |
| 5,702,358 A | 12/1997 | Witherspoon et al. |
| 5,716,386 A | 2/1998 | Ward et al. |
| 5,733,319 A * | 3/1998 | Neilson et al. ............... 606/22 |
| 5,837,003 A | 11/1998 | Ginsburg |
| 5,879,329 A | 3/1999 | Ginsburg |
| 5,975,081 A | 11/1999 | Hood et al. |
| 6,096,068 A | 8/2000 | Dobak, III et al. |
| 6,146,411 A | 11/2000 | Dae |
| 6,149,673 A | 11/2000 | Ginsburg |
| 6,149,676 A | 11/2000 | Ginsburg |
| 6,231,594 B1 | 5/2001 | Noda et al. |

OTHER PUBLICATIONS

Bruder, et al., (1998), "Influence of body temperature, with or without sedation, on energy expenditure in severe head–injured patients", *Crit Care Med* 26(3):568–572, Publisher: Department d'Anesthésie–Réanimation (Drs. Bruder, Pellissier, Courtinat, and François), CHU Timone; Hôspital d'Instruction des Armées Lavéran (Dr. Raynal), Marseille, France.

Dewitt, et al., (1998), "Accurate measurement of brain temperature", *Crit Care Med*, 26(3):431–432, Publisher: Department of Anesthesiology, University of Texas Medical Branch, Galveston, TX 77555–0830.

Henker, et al. (1998), "Comparison of brain temperature with bladder and rectal temperatures in adults with severe head injury", *Neurosurgery*, 42(5):1071–1075, Publisher: Department of Acute/Tertiary Care (RAH), School of Nursing, and Department of Neurosurgery (SDB, DWM), School of Medicine, University of Pittsburgh, Pittsburgh, Pennsylvania.

Maher and Hachinski, (1993), "Hypothermia as a potential treatment for cerebral ischemia", *Cerebrovascular and Brain Metabolism Reviews*, 5:277–300, Publisher: Department of Clinical Neurological Sciences, University of Western Ontario, London, Ontario, Canada.

Marion, et al., (1997), "Treatment of traumatic brain injury with moderate hypothermia", *The New England Journal of Medicine*, 336(8):540–546, Publisher: Brain Trauma Research Center, University of Pittsburgh Medical Center, Pittsburgh, Pennsylvania.

Rumana, et al. (1998), "Brain temperature exceeds systemic temperature in head–injured patients", *Crit Care Med*, 26(3):562–567, Publisher: Department of Neurosurgery, Baylor College of Medicine, Houston, Texas.

* cited by examiner

COOLING SYSTEM FOR INDWELLING HEAT EXCHANGE CATHETER

This is a continuation application of U.S. patent application Ser. No. 09/220,897, filed Dec. 24, 1998. now U.S. Pat. No. 6,146,411

BACKGROUND OF THE INVENTION

1. Field of the Invention

This invention relates generally to methods and apparatus for exchanging heat with the body of a patient.

2. Description of Related Art

Many advantages of hypothermia are well known. By way of example, it has been found particularly desirable to lower the temperature of body tissue in order to reduce the metabolism of the body. In stroke, trauma and several other pathological conditions, hypothermia also reduces the permeability of the blood/brain barrier. It inhibits release of damaging neurotransmitters and also inhibits calcium-mediated effects. It is also known that hypothermia inhibits brain edema and lowers intracranial pressure.

Hypothermic treatment has been typically addressed systemically, meaning that the overall temperature of the entire body has been lowered to achieve the advantages noted above. This has been particularly desirable in surgical applications where the reduced metabolism has made it possible to more easily accommodate lengthy operative procedures. An example of this systemic approach includes catheters for transferring heat to or from blood flowing within a patient's vessel, as disclosed by Ginsburg in U.S. Pat. No. 5,486,208. A closed loop heat exchange catheter is also disclosed by Saab in U.S. Pat. No. 5,624,392. A cooling device for whole-body hyperthermia that utilizes the circulatory system of the body is known to be more efficient since the entire volume of the body is constantly perfused with the cold fluid at a capillary level.

Likewise, various other means of cooling the body have been tried with cooling blankets, ice water bladder lavages, ice baths, esophageal catheters and their associated methods. All of these devices require a considerable time to cool the body since the primary heat transfer occurs through the skin or the skull. A more efficient body cooling device that can quickly cool and accurately control the body temperature is required.

BRIEF SUMMARY OF THE INVENTION

The present invention provides a heat exchange system wherein a self-contained primary cooling circuit having a first fluid circulating therein is coupled to a self-contained secondary cooling circuit in a heat exchange relationship. The two circuits are in fluid-flow isolation from each other and are provided with associated pumping mechanisms to effect fluid circulation therein. The primary circuit is in fluid communication with an indwelling heat exchange catheter adapted for insertion into the body of the patient in order to effect heat exchange with a target site in the body. The secondary circuit is cooled or warmed by a temperature control system.

In one aspect of the present invention, the temperature of the system is controlled in accordance with patient temperature determinations. This can be performed automatically, in a closed feedback loop wherein temperature readings from a probe are input to a temperature controller having inputs to at least one of the pumping mechanisms in addition to the heater or cooler of the temperature control system. The temperature controller operates in accordance with temperature control algorithms taking into account the various system and patient parameters to thereby achieve and maintain desired temperature conditions in the patient's body.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION OF THE INVENTION

A heat exchange catheter and method of operation are disclosed in copending U.S. patent application Ser. No. 09/063,984, entitled "Indwelling Heat Exchange Catheter and Method of Using Same," incorporated herein by reference in its entirety. The system of the aforementioned application is adapted to produce hypothermia or hyperthermia, typically in a selected portion of the body without substantially varying the temperature of the remaining portions of the body. The selected body portion will usually be associated with a body conduit which conveys a body fluid to the selected body portion. Of particular interest are the organs of the body which are commonly nourished and maintained by a flow of blood in the arterial system. For example, a flow of blood is introduced to the brain through the carotid artery. Of course the temperature of this blood is usually at the normal body temperature.

By positioning an indwelling heat exchange catheter in the body conduit, heat can be added to or removed from the body fluid to heat or cool the selected body portion. For example, the heat exchange catheter can be disposed in the carotid artery where the arterial blood flowing to the brain can be cooled. The flow of cooled blood to the brain reduces the temperature of the brain, thereby resulting in cerebral hypothermia. This temperature reduction can be confined to the brain or other body portion, while the remaining portions of the body maintain a generally normal body temperature. In accordance with this method, the selected body portion can be cooled to thereby provide the advantages associated with hypothermia for that body portion. The remainder of the body, such as the portions other than the brain, do not necessarily experience the reduction in temperature. Of course, selective cooling is application dependent and it should be recognized that in some situations selective cooling may give way to systemic cooling in which the temperature of the whole body of the patient is cooled using a similar approach.

Several factors are of interest in effecting heat transfer in a heat exchanger. These factors include, for example, the convection heat transfer coefficient of the two fluids involved in the heat exchange, as well as the thermal conductivity and thickness of the barrier between the two fluids. Other factors include the relative temperature differential between the fluids, as well as the contact area and residence time of the heat transfer. The Reynolds number for each fluid stream affects boundary layers, turbulence and laminar flow.

In the system of the aforementioned patent application a catheter is provided with an elongated configuration, a proximal end and a distal end, and an inner tube having a second lumen disposed within the first lumen of an outer tube. Portions of the inner tube define a first flow path extending along the second lumen, while portions of the tubes define a second flow path extending between the first tube and the second tube. In one embodiment, a plurality of hollow fibers provide fluid communication between the first and second flow paths, and a heat exchange fluid is disposed in the hollow fibers to cool the fibers.

The fluid circulated in the heat exchanger catheter of the above-described system is preferably biocompatible in order to reduce the chance of harm to the patient should inadvertent rupture and fluid leakage into the patient's body occur. Additionally, it is clear that the sterility of the fluid and tubing set needs to be maintained. Known prior art devices fall short of the high sterility standard because of their use of a single circuit to deliver cooling fluid to the patient. Specifically, in systems such as those disclosed U.S. Pat. No. 3,460,538 (Armstrong), U.S. Pat. No. 4,298,006 (Parks), U.S. Pat. No. 5,437,673 (Bauset, et al.) and U.S. Pat. No. 5,624,392 (Saab), a heat exchange means adapted for insertion into a body cavity is connected in fluid communication directly to the cooling/heating source and other support devices. This arrangement is susceptible to contamination, and it becomes necessary to maintain sterility of all the support devices if the heat exchange means is intended to be used in particularly sensitive regions such as the bloodstream of the patient. This difficult sterility standard is not problematic in for example the Armstrong patent which is limited to use in body cavities such as the intestines as accessed through the mouth or stomach, or in the Baust, et al. patent intended for insertion into the urethra. On the other hand, in the patents of Saab and Parks, where direct contact with patient blood is contemplated, severe limitations are encountered in that all the equipment must be sterile, imposing great expense in equipment and manpower.

Notwithstanding the need for localized hypothermia, there will always be those procedures which call for systemic hypothermia. Many of the advantages associated with the present invention will greatly facilitate those procedures, for example by decreasing the number and complexity of operative steps, increasing the heat transfer capacity of the device, and addressing other concerns such as the formation of blood clots.

Figure 1:
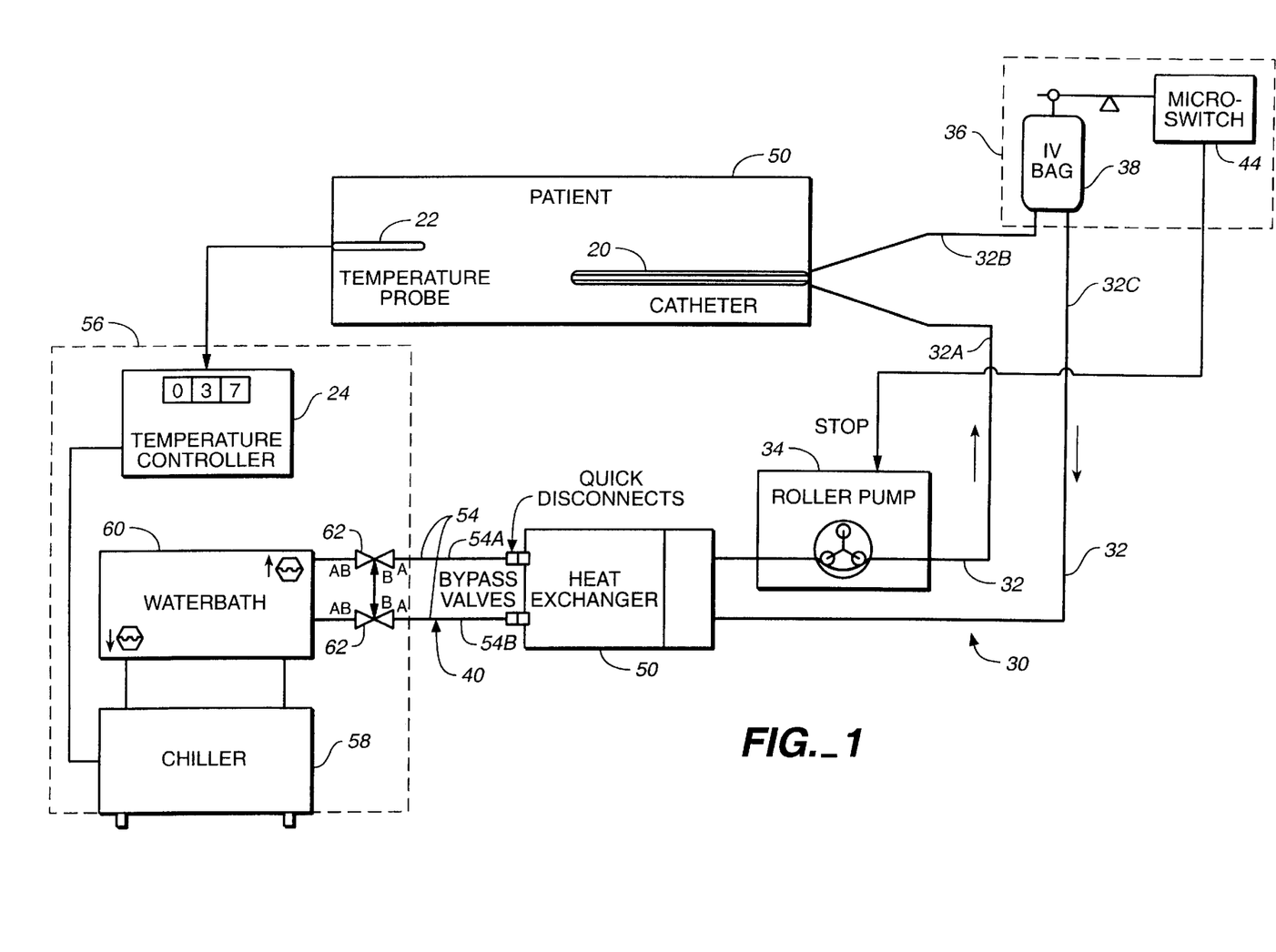
FIG. 1 is a schematic diagram of a temperature control system in accordance with the invention.

FIG. 1 diagrammatically shows a system in which a temperature control unit is shown in thermal communication with an indwelling catheter via primary and secondary fluid circuits connected in sequence. The temperature control unit and the secondary fluid circuit are self-contained and interface with the primary fluid circuit via a heat exchanger. The indwelling catheter is disposed in the body of the patient and serves to remove heat from or provide heat to at least a portion of the patient's body, although as discussed above the entire body temperature of the patient can thus be selectively altered, as is the preferred application of the present invention. The indwelling catheter is in fluid communication with a sterile tubing set having a heat exchange fluid circulating therein, with the tubing set, indwelling catheter and heat exchange fluid forming the primary fluid circuit. The temperature control module may provide automatically controlled heating or cooling in accordance with temperature measurements of the body of the patient, using a closed feedback loop, to thereby automatically achieve and maintain target temperature conditions.

As shown in FIG. 1, an indwelling catheter 20 of the type adapted for insertion into the body of the patient 50 in a particular body cavity and is preferably any one of the type of indwelling catheters disclosed in co-pending U.S. patent application Ser. No. 09/063,984 mentioned above and herein incorporated by reference in its entirety. As shown, catheter 20 is in fluid communication with a sterile tubing set 32. Catheter 20 and tubing set 32 form part of a primary fluid circuit 30 through which a first fluid is circulated in order to warm or cool a target site in the body in thermal communication with the catheter 20. It will be appreciated that the target site, such as the brain of the patient 50, may be in direct contact with the inserted catheter 20, or it may be in thermal communication with the catheter via a fluid or tissue channel such that heat transfer between the target site and the catheter 20 occurs through the fluid or tissue. For example, it is contemplated that the catheter 20 be implanted antegrade in the blood supply to the brain, with the blood, cooled by the catheter, serving to alter the temperature of the brain and blood to thereby achieve the desired benefits of hypothermia such as reducing the permeability of the blood/brain barrier, inhibiting the release of neurotransmitters, inhibiting calcium-mediated effects, inhibiting brain edema and lowering intracranial pressure. Additionally, although discussed in terms of brain surgery, it will be appreciated that the invention can be practiced in connection with surgery to different portions of a patient's body, such as for example heart bypass surgery, in which extracorporeal procedures are involved. Specifically, use of the remote control feature of the system of the invention would eliminate the requirement of constant human intervention and management of the heater/cooler to adjust temperature. A feedback loop from the heat exchanger blood outlet, or alternatively from a patient site, to the temperature controller would enable the system to self regulate the water supply to the heat exchanger at an appropriate temperature to achieve the target temperature that is entered by the operator. This strategy could be used to regulate patient temperature at a constant value or to control cooling and reheating. Preprogrammed temperature profiles can be used to control rate of change optimized for therapeutic benefit. In this manner, temperature control can be effected in procedures which involve circulation of blood outside of the body that often employ the use of heat exchangers to control the temperature of the blood thus effecting the temperature of the patient. Such procedures include ECMO (long term extracorporeal membrane oxygenation) and heart lung (cardiopulmonary) bypass surgery, which are typical examples where a heat exchanger is used not only to offset the effects of the blood circulating in tubing at room temperature but also to institute hypothermia for clinical purposes.

Pump 34 may be of conventional design, but preferably is a roller pump in order to maintain the integrity of the self-contained primary circuit and thereby preserve its sterility. Other types of pumps which may be used are diaphragm pumps, bladder pumps, piston pumps, peristaltic pumps, etc., all of which are known in the art. Pump 34 serves to circulate the first fluid through the tubing set 32 and catheter 20. Pump 34 is preferably coupled to segment 32A of primary circuit 30, although other segments can be used for this purpose. The first fluid is preferably biocompatible and is thus selected in order to minimize the harm to the patient in case of inadvertent leakage into the patient's body. Sterile water or saline are two candidate solutions, although other fluids may be used. Considerations other than biocompatibility which are to be taken into account in selecting an appropriate solution are heat transfer properties, viscosity, freezing point and compatibility with materials used, among other factors.

Figure 2:
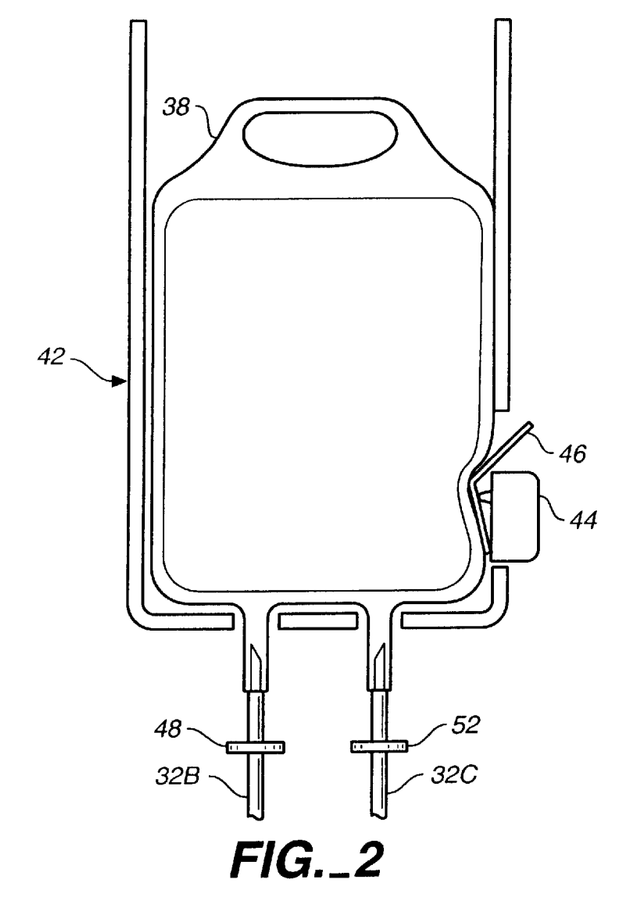
FIGS. 2 and 3 are schematic diagrams of a fluid level detector in an untriggered and a triggered state, respectively, in accordance with one aspect of the invention.
Figure 3:
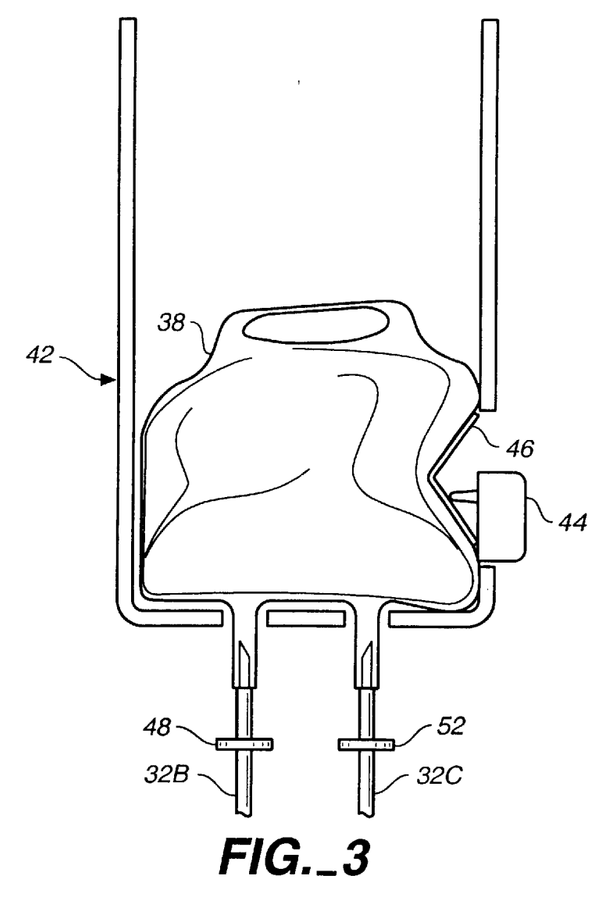
Figure 4:
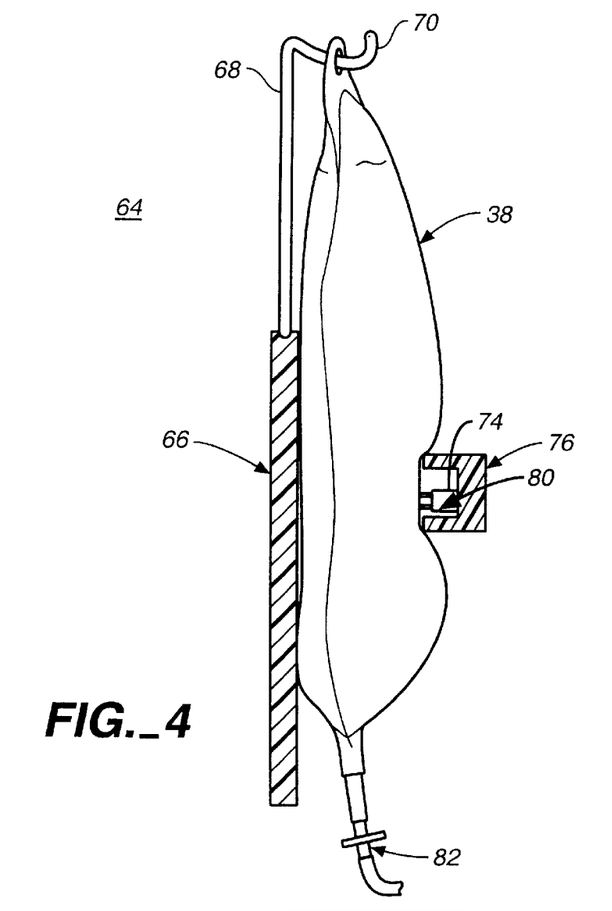
FIG. 4 is a schematic partial cross-sectional side elevational view of a fluid level detection system in accordance with a second aspect of the invention, wherein the volume reservoir is in the inflated configuration.
Figure 5:
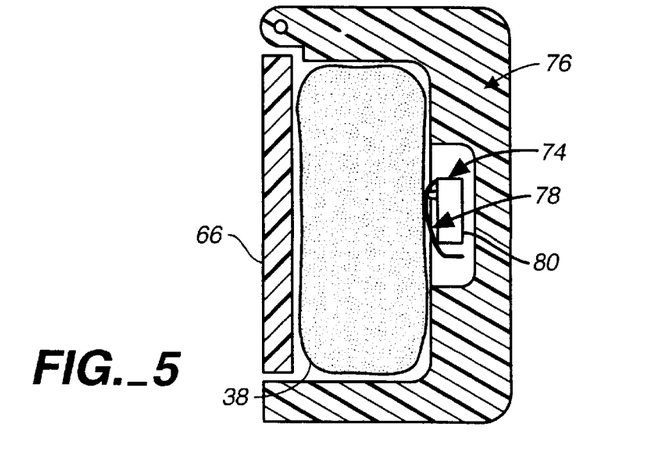
FIG. 5 is a schematic partial cross-sectional top view of the detection system of FIG. 4.
Figure 6:
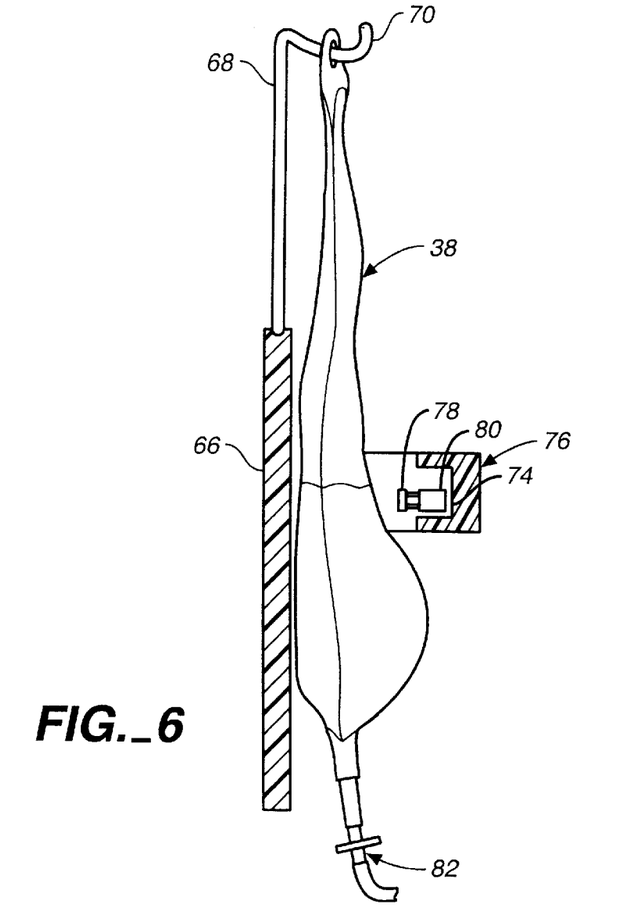
FIG. 6 is a schematic partial cross-sectional side elevational view of the detection system of FIG. 4, wherein the volume reservoir is in the deflated configuration.
Figure 7:
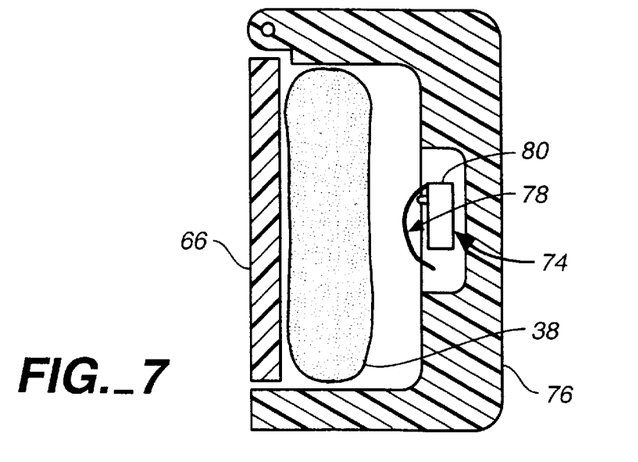
FIG. 7 is a schematic partial cross-sectional top view of the detection system of FIG. 6.

To detect fluid leakage in primary circuit 30, an arrangement in accordance with the invention utilizes a fluid level detection system 36 comprising a fluid volume reservoir, which is preferably a conventional IV (intravenous) bag (38), supported in a frame 42 in the manner shown in FIGS. 2 and 3. Intravenous bag 38 mates with segments 32B and 32C of tubing set 32 using conventional fittings 48 and 52. A switch 44 having a movable lever 46 normally biased outward in the direction of intravenous bag 38 is disposed against the intravenous bag 38 such that when the bag is at an acceptably filled level, the bag is inflated and the weight and/or pressure in the bag urges the movable lever 46 to a first position corresponding to a first state of the switch 44, while when the bag is at an unacceptably depleted level, due to fluid loss from the primary circuit 30, the bag deflates and the movable lever 46, urged by for example a spring mechanism (not shown), returns to the normal, outward-baised position which corresponds to a second state of the switch 44. At the second state switch 44 may be used to actuate pump shutoff or other corrective action, such as providing an audible or visible alarm to the operator. It will be appreciated that switch 44 can be triggered using other schemes, such as those relying on the weight of a suspended IV bag or reservoir for example, or other, known level detection devices of the optical or capacitive type, can be used in the invention without departure from the spirit and scope thereof.

FIGS. 4–7 show a second arrangement of a fluid level detection system in accordance with the invention. Frame 64 comprises a support plate 66 and a mounting pole 68 having a hook 70 at the top thereof. Mounting pole 68 and hook 70 operate to suspend a fluid volume reservoir such as IV bag 38 in the frame 64. A switch assembly 74 is mounted in a capture arm 76 which is pivotably mounted such that when the capture arm 76 is in the engaged position shown, switch lever 78 of microswitch 80 protrudes inwardly towards IV bag 38. When the bag is inflated with fluid (FIGS. 4 and 5), switch lever 78 is effectively depressed such that microswitch 80 is in a first state, while when the bag is deflated due to loss of fluid (FIGS. 6 and 7), switch lever 78, normally urged away from microswitch 80 by a biasing means such as a spring (not shown) protrudes outwards and disposes microswitch 80 in a second state. These two states can be distinguished to provide an indication of fluid level in primary fluid circuit 30 with which IV bag 38 is in fluid communication via IV spike 82 for example.

In addition to serving as a volume gain or loss detector, fluid detection system 36 provides several advantages enhancing the safe practice of the present invention. For example, the volume reservoir (IV bag 38) serves as an air trap to remove deleterious pockets of air from the primary fluid circuit 30 and as a source of priming volume to the primary fluid circuit. Additionally, the volume reservoir provides a fluid volume buffer to accommodate modulations in the primary fluid circuit 30.

Primary circuit 30 is in heat exchange relationship with a secondary circuit 40 containing a second fluid circulating therein. A sterile heat exchanger 50 is provided for this purpose and forms part of the sterile primary circuit 30. Heat exchanger 50 interfaces between the two fluid circuits and serves to facilitate heat transfer therebetween in a well known manner whose details will be omitted herein for purposes of clarity. Like tubing set 32, heat exchanger 50 of primary circuit 30 is sterile and is preferably disposable and may be integrally formed with or removably coupled to the tubing set 32. The nature of fluid pump 34 is such that the tubing set 32, along with heat exchanger 50 in the integrally-formed configuration, can be readily removed and replaced with each new patient use.

Fluid circuits 30 and 40 retain their fluids in isolation from each other in order to maintain the sterility of at least primary fluid circuit 30 and to permit the use of a non-biocompatible fluid in secondary fluid circuit 40. Advantages of non-biocompatible fluids, such as for example an anti-freeze/water mixture, include the ability to achieve temperatures below the 0°-Celcius limit imposed by water or saline, and thereby provide for a more rapid cooling down process especially at initial system start-up when component and fluid temperatures have to be rapidly lowered from their room temperature state.

Secondary circuit 40 comprises tubing set 54 having segments 54A and 54B which are preferably removably coupled to heat exchanger 50. A temperature control module 56 serves to cool or warm the second fluid circulating in tubing set 54 in a controlled manner to be described below. Temperature control module 56 is provided with a chiller 58 and a heater (not shown) which operate to controllably alter the temperature of the second fluid, either directly or via a waterbath 60 in a well known manner. Use of a heat source is preferred in order to provide for more precise control of the temperature of the second fluid, and to permit the use of the system to warm the temperature of a target site in the body of the patient, especially after a preceding cooling phase. A pump 26 (FIG. 8) circulates the second fluid through the secondary fluid circuit 40, thereby retaining the secondary circuit at the desired temperature. Because during initial startup it may be desirable to accelerate the cooling process, the efficiency of the system can be increased by provision of bypass valves 62 which at startup are utilized to restrict fluid circulation in secondary circuit 40 primarily to the fluid within module 56.

Figure 8:
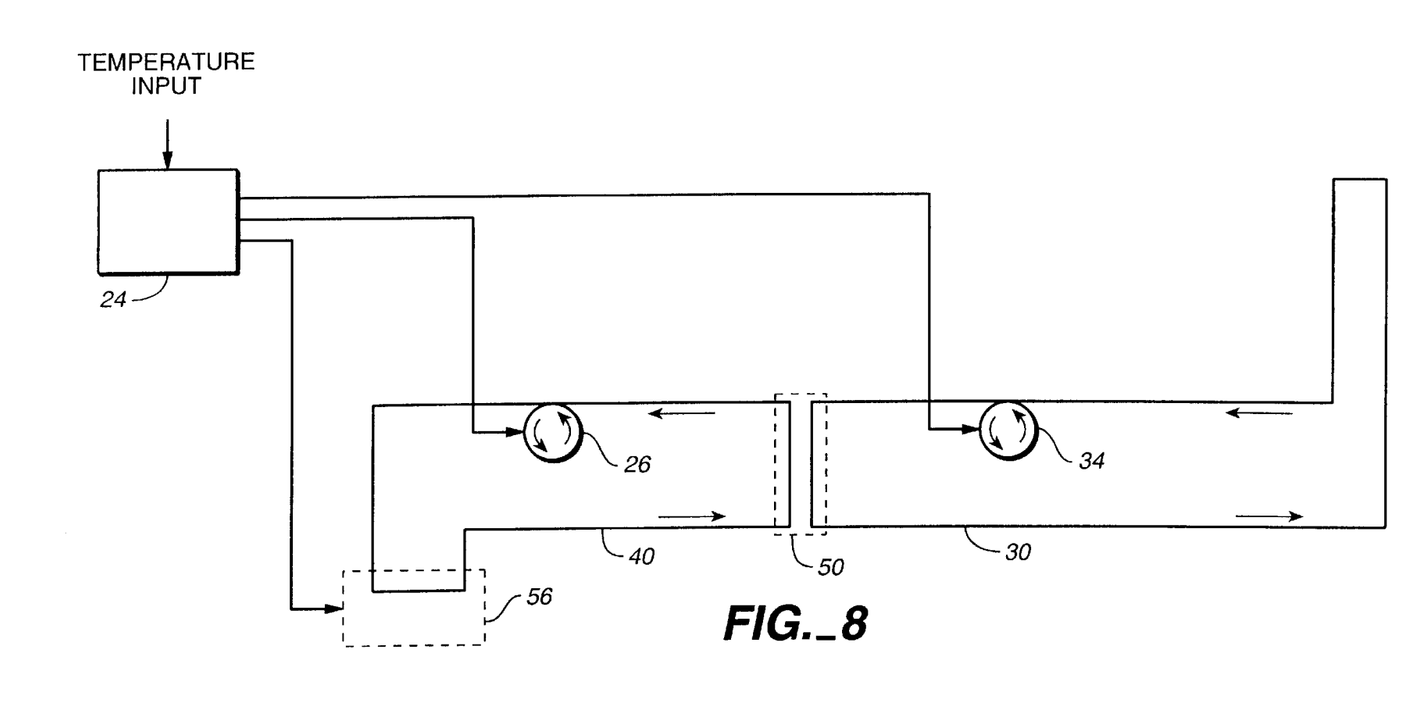
FIG. 8 is a schematic diagram showing the heat exchange control in accordance with the invention.

To provide temperature control especially during systemic cooling or heating in which it is desired to cool or warm the entire body of the patient, the patient's body temperature is measured and temperature control module 56 is operated accordingly. This may be effected manually by the operator, or automatically, using one or more temperature probes 22 (only one is shown) inserted into the body of the patient 50, rectally for example. Clearly, in the systemic heat exchange application, the temperature probes 22 need not be positioned in proximity with the site at which the indwelling catheter 20 is disposed, but rather can be placed anywhere from which a core body temperature measurement can be attained. In the automatic arrangement shown schematically in FIG. 1, the temperature measurement from probe 22 is provided as feedback in a closed loop to a proportional temperature controller 24. Any suitable processing device can operate as the proportional temperature controller 24 and serves to control the temperature of the second fluid by controlling the amount of cooling or heating to which the second fluid of secondary circuit 40 is subjected. Proportional temperature controller 24 can also be used to adjust the circulation rates in the primary and/or secondary circuits in accordance with the temperature measurement signals from probe 22. Such adjustment can be effected using direct control of the pumping rates of pumps 26 and 34 as shown in FIG. 8. Proportional temperature controller 24 is programmed with appropriate time constants based on the location of probe 22 in the patient's body and the corresponding temperature response time of the system and the body. As mentioned above, probe 22 can be placed anywhere in the body and is not necessarily restricted to proximity to the target site, as long as the correlation between the temperature at the actual probe location and that at the target site is known. One example of such a correlation is the knowledge that arterial blood temperature will ultimately determine brain temperature, and the relationship between these two can be used to program the temperature control algorithm employed by the proportional temperature controller 24 to achieve a target temperature or temperature range in the brain. Similarly, a plurality of probes 22 can be used to provide feedback to proportional temperature controller 24, with some or even all of these probes being placed exteriorly of the body at various locations in the system—for example, at the primary and/or secondary circuits 30 and 40. Control over such an arrangement can be effected if the relationship of the various fluid circuits and components of the system can be properly correlated to that of the patient 50, with parameters such as patient weight, height, temperature, circulatory rate, etc. being taken into account to ensure safe and proper operation.

As mentioned above, the invention can be practiced in connection with surgery to various parts of the body and is not restricted to surgery to the brain. For example, the system of the invention can be used to provide auto feedback and temperature control during heart bypass surgery, or during other types of surgery as one of ordinary skill in the art will appreciate.

In accordance with the invention, the feedback scheme of the invention can be used to maintain desired temperature conditions for a patient. Specifically, the system can be used to control any temperature deviations from an acceptable temperature range, which may be a normothermic range, whereby probes 22 will trigger cooling or heating of the patient's body depending on this sensed deviation. Moreover, since this deviation is generally indicative of certain physiological activity of which the physician should be apprised, the operation of the system can be used as an indication that this physiological activity is taking place. For instance, when the cooling operation of temperature control module 56 is triggered due to a rise in the patient's core body temperature, the system cooling activity, as reflected in the increased workload of the cooling componentry of the system, is then used to indicate to the physician, audibly or visibly using an alarm or other status indicator device (not shown), that the patient's body is attempting to enter a fever state. Appropriate measures can then be taken. Of course, parameters other than workload can be used to provide this indication, such as the slope of the temperature feedback along with the sign of the slope.

The above are exemplary modes of carrying out the invention and are not intended to be limiting. It will be apparent to one of ordinary skill in the art that modifications thereto can be made without inventive departure from the spirit and scope of the invention as set forth in the following claims.

What is claimed is:

1. An apparatus for changing and maintaining the temperature of at least a portion of the body of a patient, the apparatus comprising:

an indwelling catheter adapted for heat exchange within the body;

a means for measuring a core body temperature of the patient;

a primary fluid circuit in fluid flow communication with the indwelling, catheter, the primary circuit adapted to contain a first circulating fluid therein and provided with a detector for sensing fluid loss;

a secondary fluid circuit which is in heat exchange relationship with the primary fluid circuit and adapted to contain a second circulating fluid therein, the first and second fluids being in fluid-flow isolation from each other; and a temperature control module for changing the temperature of the second fluid, whereby, the temperature control module operates depending on the measured core body temperature of the patient;

wherein the detector for sensing fluid loss comprises:

a fluid volume reservoir in fluid communication with the primary circuit, the fluid volume reservoir assuming a first configuration when the first fluid level is at an acceptable level and assuming a second configuration when the first fluid level is at an unacceptable level;

a switch adapted to toggle between first and second states depending on the configuration of the fluid volume reservoir.

2. The apparatus of claim 1, wherein the switch initiates corrective action when at one of the first and second states.

3. The apparatus of claim 2, wherein the fluid volume reservoir is in an inflated configuration when the first fluid level is at an acceptable level and is in a deflated configuration when the first fluid level is at an unacceptable level, and wherein the switch is provided with a movable actuating lever biased against the fluid volume reservoir such that the lever causes the switch to toggle between the first and second states depending on the configuration of the fluid volume reservoir.

4. A system for changing the body temperature of a patient, the system comprising:

an indwelling catheter adapted for heat exchange with the body of the patient;

a means for measuring a core body temperature of the patient;

a primary fluid circuit in fluid communication with the indwelling catheter, the primary fluid circuit adapted to contain a first circulating fluid therein and provided with a detector for sensing fluid loss; and a temperature control module connected with the means for measuring a core body temperature of a patient for automatically changing the temperature of the first circulating fluid in accordance with the core body temperature of the patient;

wherein the detector for sensing fluid loss comprises:

a fluid volume reservoir in fluid communication with the primary circuit, the fluid volume reservoir assuming a first configuration when the first fluid level is at an acceptable level and assuming a second configuration when the first fluid level is at an unacceptable level;

a switch adapted to toggle between first and second states depending on the configuration of the fluid volume reservoir.

5. The system of claim 4, wherein the switch initiates corrective action when at one of the first and second states.

6. The system of claim 5, wherein the fluid volume reservoir is in an inflated configuration when the first fluid level is at an acceptable level and is in a deflated configuration when the first fluid level is at an unacceptable level, and wherein the switch is provided with a movable actuating lever biased against the fluid volume reservoir such that the lever causes the switch to toggle between the first and second states depending on the configuration of the fluid volume reservoir.

7. An apparatus for changing or maintaining the temperature of at least a portion of a body of a patient, the apparatus comprising:
- means for exchanging heat with the portion of the body;
- a means for measuring a core body temperature of the patient;
- a primary fluid circuit in fluid communication with the means for exchanging heat, the primary circuit adapted to contain a first circulating fluid therein and provided with a detector for sensing fluid loss;
- a secondary fluid circuit in beat exchange relationship with the primary fluid circuit and adapted to contain a second circulating fluid therein, the first and second fluids being in isolation from each other; and
- a means for changing the temperature of the second fluid connected with the means for measuring a core body temperature;
- wherein the detector for sensing fluid loss comprises:
  - a fluid volume reservoir in fluid communication with the primary circuit, the fluid volume reservoir assuming a first configuration when the first fluid level is at an acceptable level and assuming a second configuration when the first fluid level is at an unacceptable level;
  - a switch adapted to toggle between first and second states depending on the configuration of the fluid volume reservoir.

8. The apparatus of claim 7, wherein the switch initiates corrective action when at one of the first and second states.

9. The apparatus of claim 8, wherein the fluid volume reservoir is in an inflated configuration when the first fluid level is at an acceptable level and is in a deflated configuration when the first fluid level is at an unacceptable level, and wherein the switch is provided with a movable actuating lever biased against the fluid volume reservoir such that the lever causes the switch to toggle between the first and second states depending on the configuration of the fluid volume reservoir.

10. A system for changing the body temperature of a patient, the system comprising.
- a means for exchanging heat with the body of the patient;
- a means for measuring a core body temperature of the patient;
- a primary fluid circuit in fluid communication with the means for exchanging heat, the primary circuit adapted to contain a first circulating fluid therein and provided with a detector for sensing fluid loss;
- a means for automatically changing the temperature of the first fluid in accordance with the core body temperature of the patient such that a desired body temperature is approached;
- wherein the detector for sensing fluid loss comprises;
  - a fluid volume reservoir in fluid communication with the primary circuit, the fluid volume reservoir assuming a first configuration when the first fluid level is at an acceptable level and assuming a second configuration when the first fluid level is at an unacceptable level;
  - a switch adapted to toggle between first and second states depending on the configuration of the fluid volume reservoir.

11. The system of claim 10, wherein the switch initiates corrective action when at one of the first and second states.

12. The system of claim 11, wherein the fluid volume reservoir is in an inflated configuration when the first fluid level is at an acceptable level and is in a deflated configuration when the first fluid level is at an unacceptable level, and wherein the switch is provided with a movable actuating lever biased against the fluid volume reservoir such that the lever causes the switch to toggle between the first and second states depending on the configuration of the fluid volume reservoir.

* * * * *